(12) United States Patent
Schaffer et al.

(10) Patent No.: US 9,188,562 B2
(45) Date of Patent: Nov. 17, 2015

(54) SILVER TESTING APPARATUS

(71) Applicant: FMS Technologies, LLC, Hamburg, PA (US)

(72) Inventors: Jarrett Schaffer, Allentown, PA (US); Gerald Petrole, Sr., Tamaqua, PA (US)

(73) Assignee: FMS Technologies, LLC, Hamburg, PA (US)

( * ) Notice: Subject to any disclaimer, the term of this patent is extended or adjusted under 35 U.S.C. 154(b) by 301 days.

(21) Appl. No.: 13/905,844

(22) Filed: May 30, 2013

(65) Prior Publication Data

US 2013/0319879 A1    Dec. 5, 2013

Related U.S. Application Data

(60) Provisional application No. 61/653,587, filed on May 31, 2012.

(51) Int. Cl.
  *G01N 27/413*  (2006.01)
  *G01N 27/416*  (2006.01)
  *G01N 33/20*   (2006.01)

(52) U.S. Cl.
  CPC ............ *G01N 27/413* (2013.01); *G01N 27/416* (2013.01); *G01N 33/20* (2013.01)

(58) Field of Classification Search
  CPC .... G01N 27/413; G01N 27/116; G01N 33/20
  See application file for complete search history.

(56) References Cited

U.S. PATENT DOCUMENTS

| | | | | |
|---|---|---|---|---|
| 5,888,362 | A  * | 3/1999  | Fegan, Jr. ........................ | 204/400 |
| 7,005,306 | B1 * | 2/2006  | Poris ................................ | 438/17  |
| 2004/0142483 | A1* | 7/2004  | Genshaw ........................ | 436/164 |
| 2007/0239921 | A1* | 10/2007 | Toorians et al. ............... | 710/306 |
| 2008/0201095 | A1* | 8/2008  | Yip et al. ........................ | 702/85  |
| 2009/0089633 | A1* | 4/2009  | Hirota ............................ | 714/721 |
| 2010/0193358 | A1* | 8/2010  | Hamada ......................... | 204/547 |

* cited by examiner

*Primary Examiner* — Jennifer Dieterle
(74) *Attorney, Agent, or Firm* — Miller Law Group, PLLC

(57) ABSTRACT

A precious metal testing apparatus determines the percentage content of precious metal in a specimen being tested by detecting the change in the rate of current flow through a resistive layer formed on the specimen by an application of a corrosive electrolyte on the specimen. The electrical circuit forms a fixed resistance circuit and a variable resistance circuit due to the formation of a growing resistive layer on the specimen such that the flow of current through the variable resistance circuit decreases as the flow of current through the fixed resistance circuit increase. The detection of the rate of change in current flow as a result of the increasing growth of the resistive layer can be compared to a look-up table that provides a corresponding percentage of precious metal in the specimen. Calibration of the testing apparatus can be accomplished with a specimen of known purity of the precious metal.

15 Claims, 5 Drawing Sheets

SILVER TESTING APPARATUS

CROSS-REFERENCE TO RELATED APPLICATIONS

This application claims domestic priority on U.S. Provisional Patent Application Ser. No. 61/653,587, filed on May 31, 2012, the content of which is incorporated herein by reference.

BACKGROUND OF THE INVENTION

The present invention relates generally to an apparatus for testing the purity of precious metals, and, more particularly, to a testing apparatus that identifies the silver content in a specimen being tested by the apparatus.

A precious metal testing apparatus is shown in U.S. Pat. No. 5,888,362, issued to Lloyd V. Fegan, Jr., on Mar. 30, 1999. This testing apparatus provides a portable device that can provide accurate analysis of the quality of the precious metal, particularly gold and platinum, being tested by utilizing a hand-held probe having an electrode embedded in an electrolyte contained within a reservoir formed in the probe. The testing apparatus generates a galvanic current through the metal being tested from a battery, the strength of the current being proportionate to the quality of the precious metal being tested. In the Fegan patent, a meter circuit measures the extent of galvanic action of dissimilar metals in the presence of an electrolyte, one of the metals being the sample being tested for quality. Thus, the invention is useful for testing the metal content of gold coins, art objects jewelry, and the like, by reason that the probe can simply be touched against the object being tested to provide a reading representing the quality of the precious metal in the object.

The hand-held probe in the aforementioned precious metal testing apparatus is typically in the form of a pen having a fibrous tip from which a small amount of electrolyte is deposited onto the object being tested. The meter attached to the probe continuously measures the strength of the galvanic current and compares the result with a known point of reference for the type of precious metal being tested, whereby the percentage of precious metal within the object being tested will be known. This measurement process by the meter and pen is completed within a few hundredths of a second, thus providing an efficient manner in which the quality of precious metal can be determined. However, even though the measurement process is fast, the strengths of the galvanic reaction when reacted with gold or platinum are very weak.

The Fegan gold testing apparatus, however, is not very effective in testing for the content of silver in an object. Silver is highly conductive and the current from the pen probe easily passes through the silver specimen causing the needle to bottom out. Other known methods of testing for silver involves exposing the silver (AG) samples to a chemical test. The concentration (i.e. the purity) of the silver in the specimen is the based on a visual inspection of the chemical reaction reflecting a change in color of the exposed chemical. Such visual inspection tests can be somewhat subjective and the accuracy of the test is dependent on the experience of the person conducting the chemical test.

It would be desirable to provide an electronic apparatus that would provide an accurate and efficient testing of a specimen to be able to determine the concentration of the silver content within the sample.

SUMMARY OF THE INVENTION

It is an object of this invention to provide a testing apparatus operable in conjunction with precious metals to determine the percentage of content of the precious metal in the object being tested.

It is another object of this invention to provide a precious metal testing apparatus that can be utilized to test a precious metal other than gold.

It is a feature of this invention that the percentage content of silver can be determined in a sample being tested.

It is another feature of this invention that the calculation of the percentage content of precious metal in a sample being tested is based on a measurement of the rate of change of current or voltage through the test specimen as a resistive layer is established between the probe and the specimen being tested.

It is an advantage of this invention that the test probe causes the formation of a resistive layer on the sample being tested which changes the rate at which current flows from the probe through the sample being tested to the monitor displaying the test results.

It is another advantage of this invention that the growth of the resistive layer is a function of the percentage content of precious metal within the specimen being tested.

It is still another feature of this invention that the changes in the rate of current flowing from the probe through the resistive layer on the specimen being tested can be detected and compared with a look-up table that provides a corresponding percentage content of precious metal present in the specimen being tested.

It is another advantage of this invention that the probe carries a supply of an electrolyte that corrodes the precious metal being tested in a selected specimen.

It is yet another feature of this invention that the probe carries a supply of a saturated solution of ammonium chloride that forms silver oxide from corrosion of the silver content in a specimen being tested.

It is yet another advantage of this invention that the layer of silver oxide created by the application of an electrolyte to cause corrosion in the specimen being tested impedes the flow of current through the specimen.

It is still another object of this invention to provide an electrical circuit that utilizes Kirchhoff's law to determine the changes in the rate of current flow through the resistive layer growing on a specimen containing precious metal being tested.

It is a further feature of this invention that the detection circuit in the tester establishes a portion of the circuit that has a fixed value resistance and a portion of the circuit that forms a variable resistance due to the formation of the resistive layer on the specimen being tested.

It is further advantage of this invention that the increase in the variable resistance portion of the electrical circuit due to the growth in the formation of the resistive layer from the corrosion of the precious metal in the specimen being tested results in a decrease in the current through the variable resistance portion of the circuit and a corresponding increase in the current flowing through the fixed resistance portion of the electrical circuit.

It is still a further feature of this invention that the testing apparatus can be calibrated using a sample having a known content of precious metal being tested.

It is still a further advantage of this invention that the sample having a known content of precious metal can be a specimen formed of sterling silver.

It is another feature of this invention that the display for the testing apparatus can provide an LED indication of several parameters, including the status of the testing apparatus, such as power on, ready for testing, battery status, the ability of the testing apparatus to conduct subsequent tests, and the number of tests that can be conducted before another calibration is required.

It is still another feature of this invention that the LED display can also provide an indication of the percentage of precious metal content in the specimen being tested.

It is yet another feature of this invention that the microprocessor in the testing apparatus terminates power to the probe after conducting a test of a specimen.

It is yet another advantage of this invention that the termination of power to the probe after completing a test of a specimen allows the accumulated charge within the probe to be dissipated before providing an indication of the apparatus being ready to conduct another test.

It is a further object of this invention to utilize the rate of change of the flow of current through a specimen being tested due to the increasing growth of a resistive layer created by the application of a corrosive electrolyte on the specimen where the growth of the resistive layer is proportional to the percentage content of a precious metal within the specimen, to ascertain through comparison with a look-up table comparing various rates of change in current flow corresponding to percentage content of precious metal the percentage of precious metal content within the specimen being tested.

It is still a further object of this invention to provide4 a method of testing a specimen containing a percentage content of precious metal involving an evaluation of the rate of change in the flow of electrical current through the specimen where a resistive layer is growing as a result of an application of a corrosive electrolyte on the specimen and where the growth of the resistive layer is proportionate to the percentage content of the precious metal within the specimen.

It is a further feature of this invention that the method of testing by analyzing the rate of change of electrical current flowing through a specimen having a resistive layer growing thereon is particularly adapted for use in testing silver content in a specimen containing a percentage content of silver.

These and other objects, features and advantages can be accomplished according to the instant invention by providing a precious metal testing apparatus that determines the percentage content of precious metal in a specimen being tested by determining the change in the rate of current flow through a resistive layer formed on the specimen being tested by the application of a corrosive electrolyte on the specimen. The electrical circuit forms a fixed resistance circuit and a variable resistance circuit due to the formation of a growing resistive layer on the specimen such that the flow of current through the variable resistance circuit decreases as the flow of current through the fixed resistance circuit increase. The detection of the rate of change in current flow as a result of the increasing growth of the resistive layer can be compared to a look-up table that provides a corresponding percentage of precious metal in the specimen. Calibration of the testing apparatus can be accomplished with a specimen of known purity of the precious metal.

BRIEF DESCRIPTION OF THE DRAWINGS

The advantages of this invention will be apparent upon consideration of the following detailed disclosure of the invention, especially when taken in conjunction with the accompanying drawings wherein:

FIG. 4A is a schematic representation of the variable resistance network depicted in FIG. 4.

DETAILED DESCRIPTION OF THE PREFERRED EMBODIMENT

Figure 1:
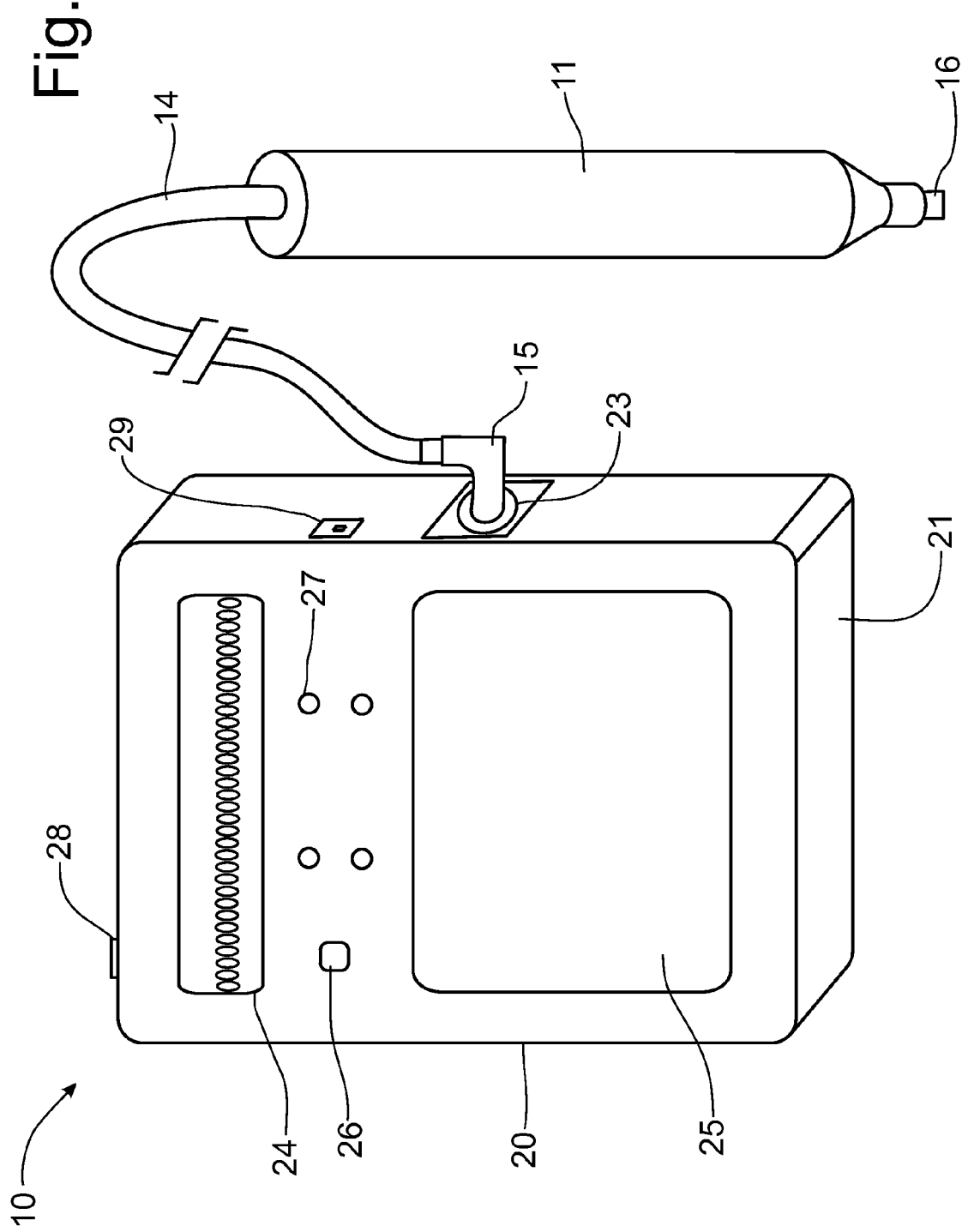
FIG. 1 is a schematic diagram of a testing apparatus incorporating the principles of the instant invention and including a pen probe electrically coupled to a meter to test the concentration of silver within the specimen being tested.
Figure 2:
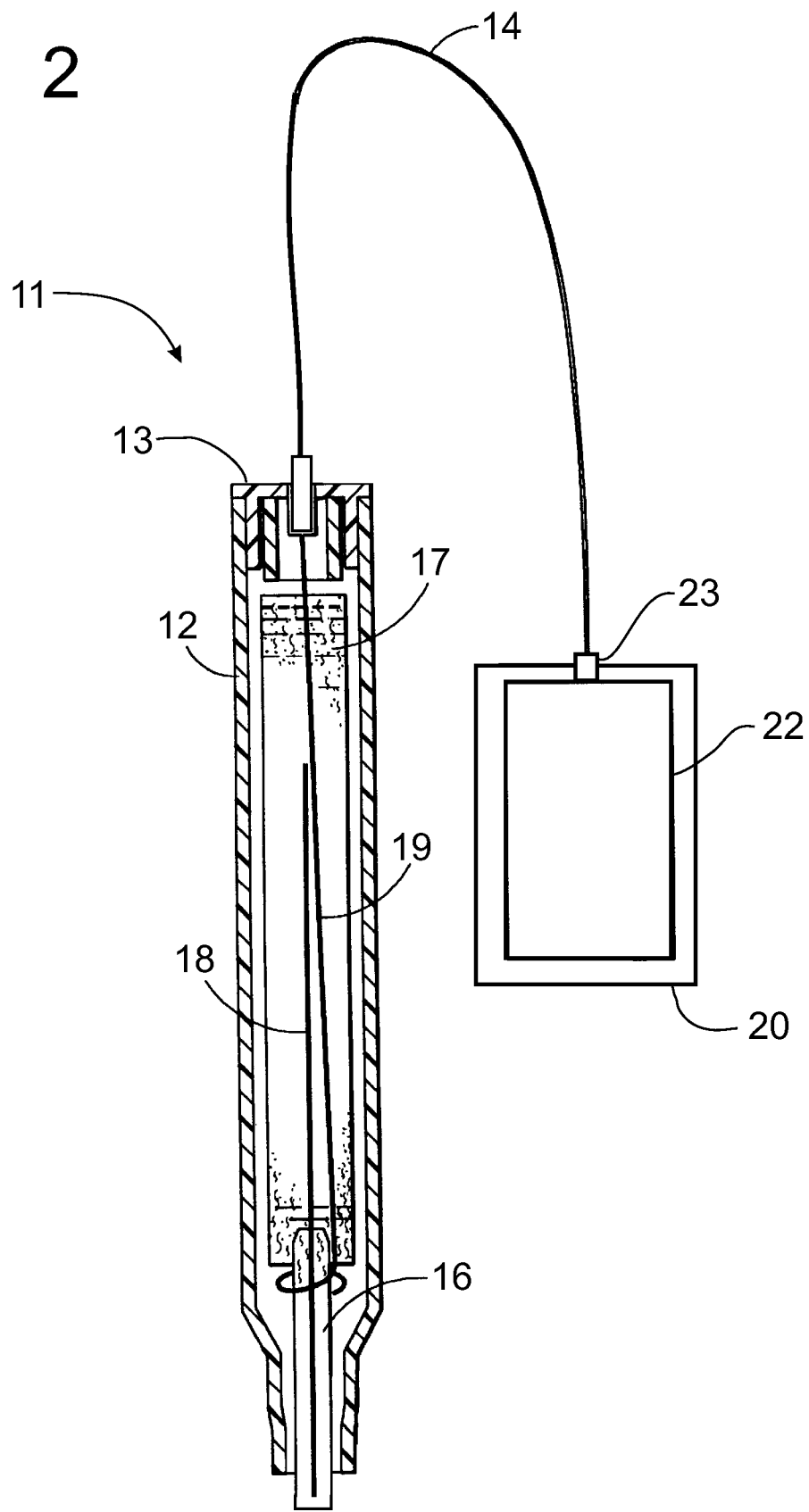
FIG. 2 is a vertical cross-sectional view of a pen probe forming a part of the testing apparatus incorporating the principles of the instant invention.
Figure 3:
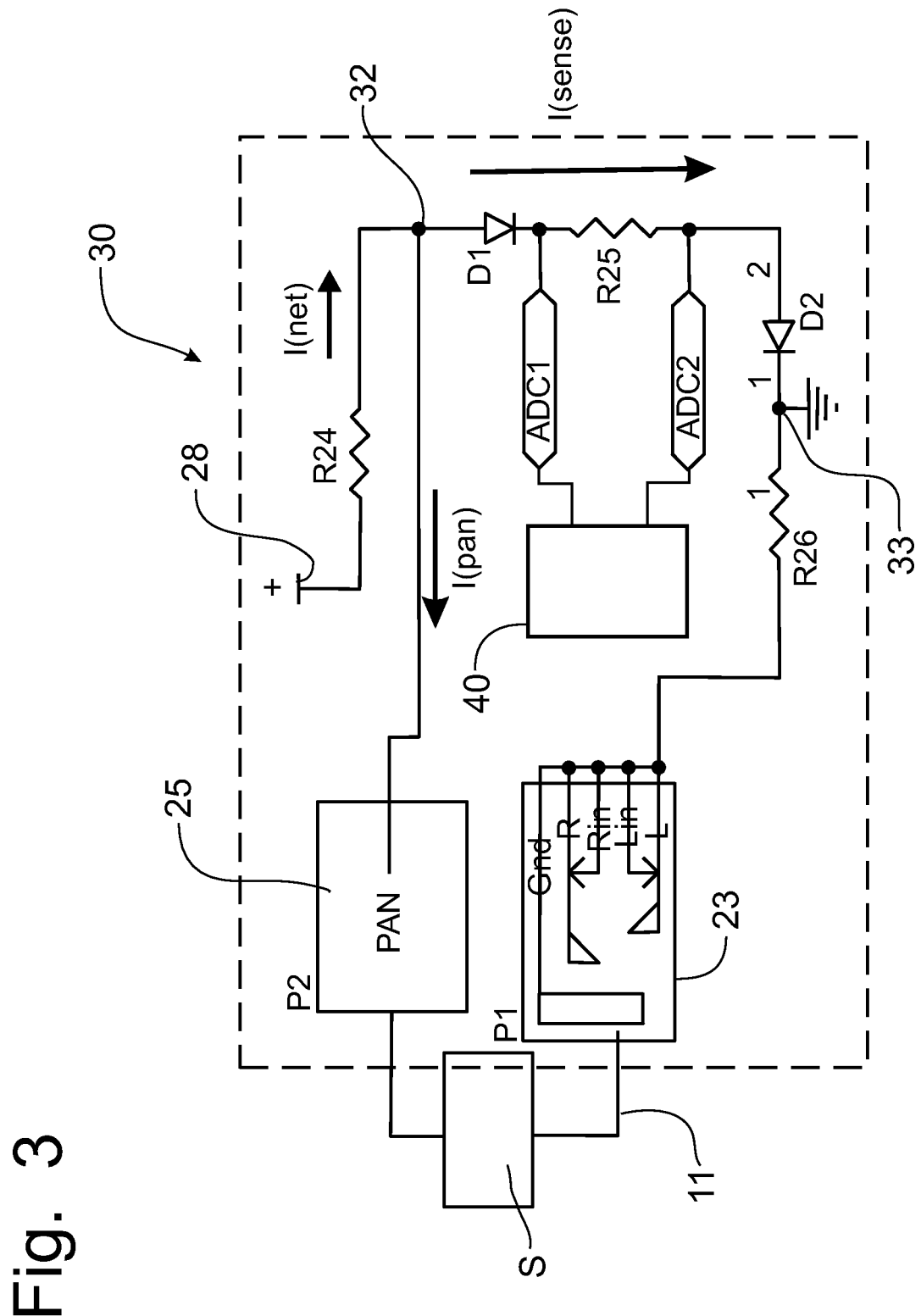
FIG. 3 is a schematic view of the electronic circuit forming the apparatus measuring the purity of silver in a test specimen.

Referring now to FIGS. 1-3, a testing apparatus for analyzing the concentration or purity of silver within a specimen being tested can best be seen. This testing apparatus 10 incorporates the principles of the instant invention.

In general, the testing apparatus 10 is used to analyze the concentration of silver, but is believed to be operable in conjunction with testing the content of gold or possibly other precious metals, such as platinum, and is based on measuring the rate of change of current or voltage shift through the test specimen as a resistive layer is established between the probe and the specimen being tested.

An exemplary embodiment of the pen probe 11 forming part of the testing apparatus 10 is shown in FIG. 2, which is a cross-sectional view of the exemplary hand-held pen probe 11. The pen probe 11 is preferably formed with a generally cylindrical body 12, which can be made of plastic or other substantially electrically non-conductive material. A top cap 13 is coupled to an electrical wire 14 fitted with a jack 15 to facilitate a detachable electrical connection of the pen probe 11 to the circuitry 30 within the meter 20. The end of pen probe 11, which is placed into contact with the specimen to be tested, is formed as a fiber tip 16 that is in communication with a reservoir 17 containing a supply of electrolyte, such as a saturated solution of ammonium chloride, or other solutions that will be operable to form a resistive layer on the specimen being tested.

The fiber tip 16 is preferably provided with a thin platinum wire 18, which is preferably embedded into the fiber tip 16 and extends into the reservoir 17. A second thin platinum connecting wire 19 couples the platinum wire 18 to the wire 14 at the top cap 13 of the pen probe 11. The wires 18, 19 provide for the passage of electrical current into the electrolyte which is absorbed into the fiber tip 16 and is deposited onto the specimen being tested. The testing apparatus 10 further includes a meter 20 including a housing 21 in which is mounted a printed circuit board 22 including a port 23 to which the jack 15 can be detachably connected. Also electrically connected to the circuitry 22 is a test pad 25 that is preferably formed as a copper pour having a surface coating of gold.

The meter 20 is also constructed with a light-emitting diode (LED) indicator bar 24 that reflects the results of the testing of the sample, as will be discussed in greater detail below. In addition, the housing 21 supports a calibration switch 26 that is operable to initiate the calibration procedure, as will also be described in greater detail below. The housing 21 can also support other LEDs that reflect the status of the operation of the testing apparatus 10, such as a ready light 27, a power-on light, a battery status light, etc. The meter 20 can also have a three position on/off switch 29 that is movable to an off position, an external power position, and a battery power position. The housing 21 also supports a port 28 for connection to a source of external power, such as 110 VAC electrical current through the use of an adapter (not shown).

The electronic circuitry 30 is reflected in the schematic diagram of FIG. 3. Either a battery (not shown) or a source of external electrical power connected through the port 28 provides an electrical current $I_{net}$ into the circuitry 30. The current $I_{net}$ reaches the node 32 and is divided into a first current flow $I_{pan}$ and a second current flow $I_{sense}$. With the silver specimen S placed on the test pan 25 and the probe 11 touching the silver specimen S a circuit is completed for the passage of $I_{pan}$ and $I_{sense}$ to ground 33. Because the initial resistance of the silver specimen S is minimal, the current $I_{pan}$ is substantially greater than the current $I_{sense}$ which must pass through the diode D1, diode D2 and the resister R25 to reach ground 33.

Figure 4:
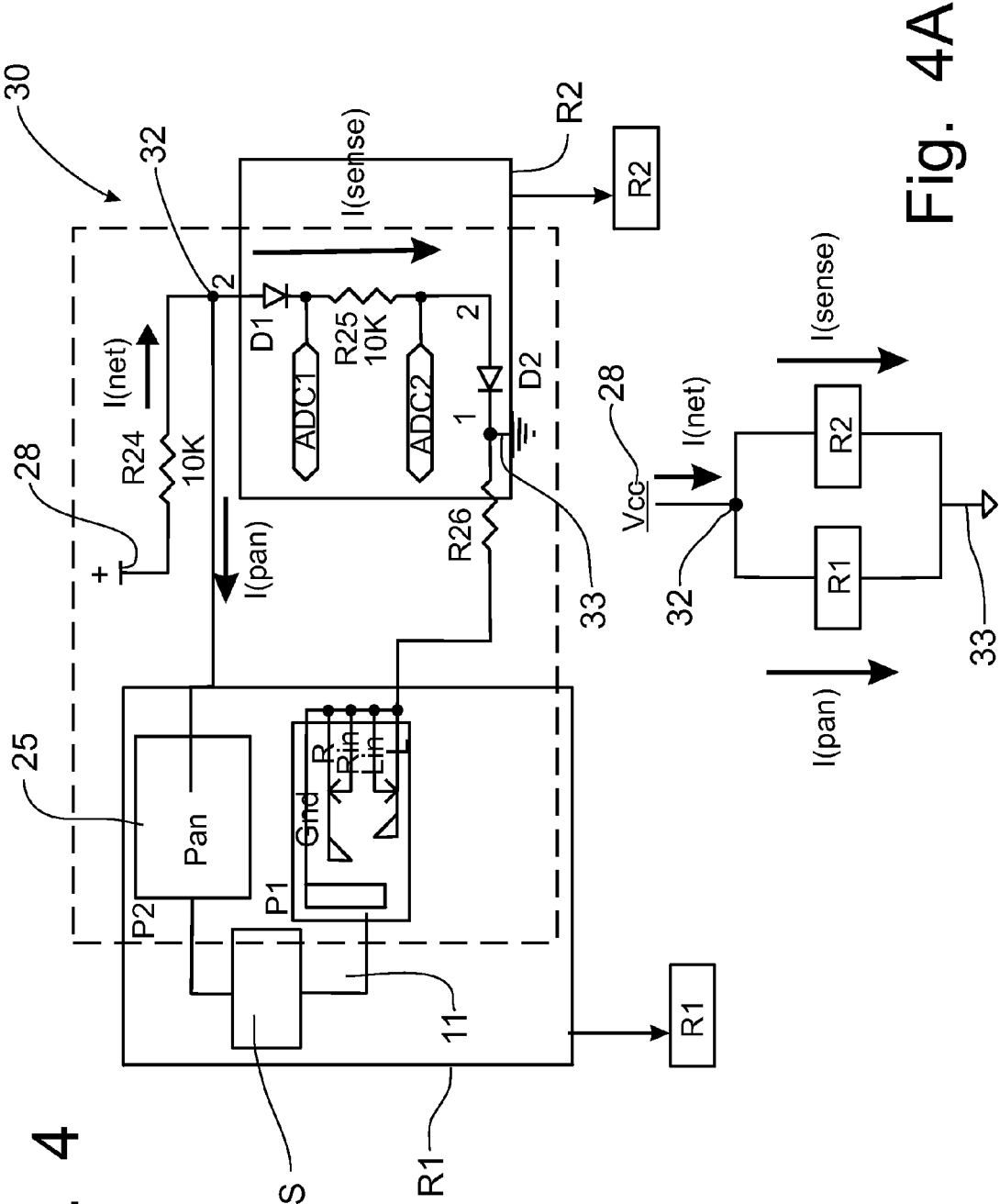
FIG. 4 is a schematic view of the electronic circuit depicted in FIG. 3 but modified to show the operative principle of the instant invention.

As the probe 11 touches the silver specimen S, the electrolyte in the probe 11 deposits on the silver specimen S and starts corroding the adjacent surface of the silver specimen S by forming silver oxide between the fiber tip 16 and the silver specimen S. The layer of silver oxide is a resistive layer that impedes the flow of electrical current. Thus, as the layer of silver oxide increases, the current $I_{pan}$ decreases and, due to Kirchhoff's law, the current $I_{sense}$ increases. The principle is demonstrated in FIGS. 4 and 4A. Essentially, the pan 25, silver specimen S and probe 11 form a variable resistance R1 due to the growing layer of silver oxide between the probe 11 and the silver specimen S. The portion of the circuitry 30 between the node 2 and the ground 33, which includes the diode D1, the resister R25 and the diode D2, is a fixed value resistance. As the variable resistance R1 increases with the building of the silver oxide layer, the current $I_{pan}$ decreases, resulting in the current $I_{sense}$ increasing.

Figure 5:
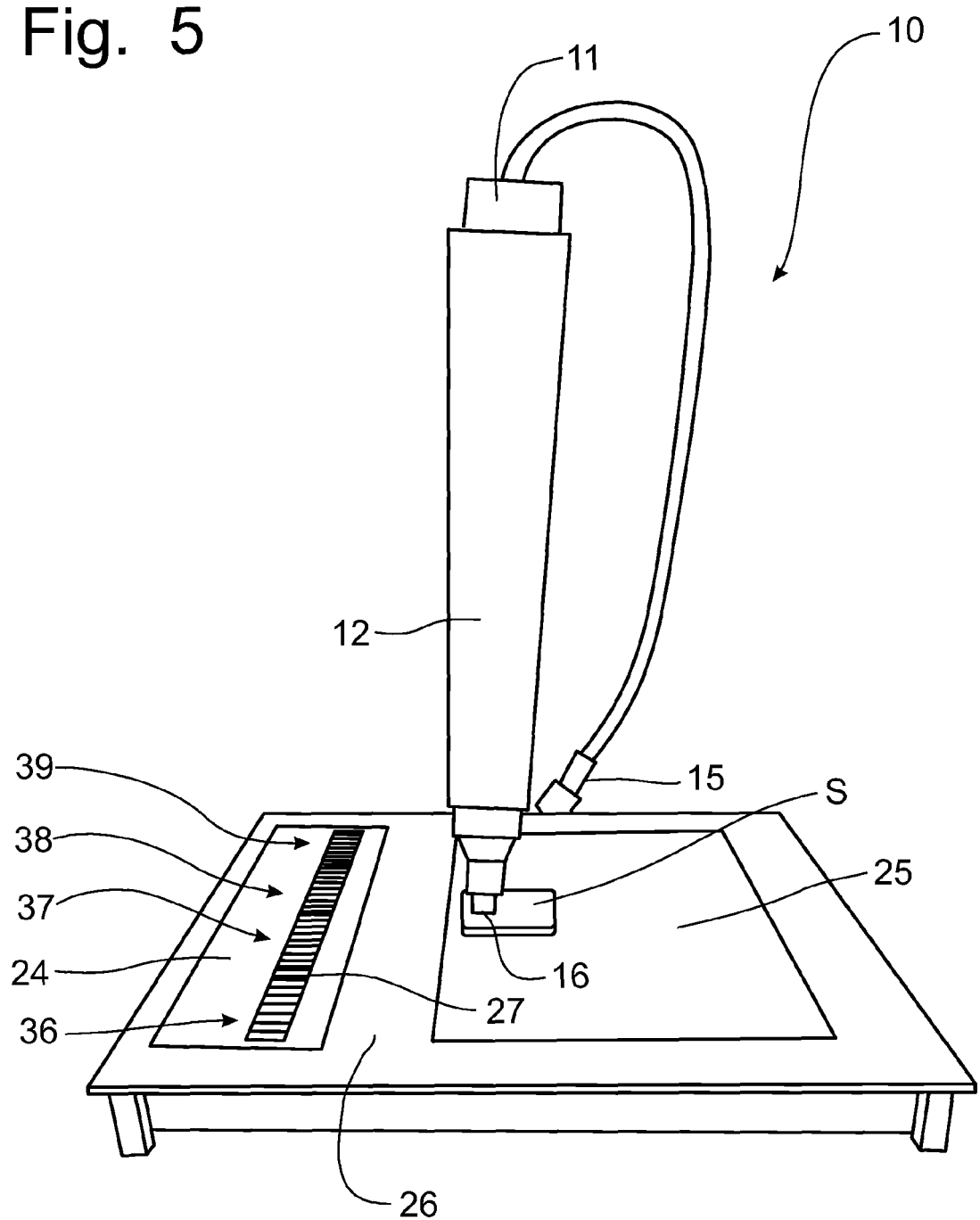
FIG. 5 is a photograph of a prototype of the testing apparatus in operation testing the concentration of silver content in a test specimen on the pan of the test apparatus.

A prototype of the testing apparatus 10 is depicted in FIG. 5 where the fiber tip 16 of the probe 11 is in contact with the silver specimen S, seated on the pan 25. The LED indicator bar 24 is divided into four sets of LEDs, although in the commercial embodiment all four sets of lights will not likely be required. In the first set 36 of LEDs, the lights cycle as the tests, as described in greater detail below are conducted. The first set 36 of LEDs provide an indication that the testing is being conducted. The second set 37 of LEDs provides an indication of the charge remaining in the pen probe 11 with the second set 37 of LEDs providing a visual indication of the status of the pen probe 11 as far as conducting a subsequent test. Associated with the second set 37 of lights is the ready light 27 that provides a reinforcement of the status of the pen probe 11 to conduct another test.

The third set 38 of LEDs is the concentration indicator with each respective LED indicating a different concentration or purity of silver in the silver specimen S. For example, the LED at one end could indicate 99.99% silver content, the next LED 95% silver content, the next LED 92.5% silver content (which is sterling silver), the next LED 90% and the last LED perhaps less than 80% silver. Between the second set 37 and the third set 38 of LEDs, a red LED could be used to provide an indication that no silver content was found during the test. The fourth set 39 of LEDs could be used to provide a count down of tests before a new calibration of the apparatus 10 is required.

Referring again to FIG. 1, the ADC1 and ADC2 sensors provide a reading of the current $I_{sense}$ on opposite sides of the resister R25. The test procedure operates to take a predetermined number of readings by the sensors ADC1 and ADC2 which are sent to the microprocessor 40 which calculates the rate of increase in the current $I_{sense}$. The average rate of increase over the predetermined number of readings being taken is then compared to a calibration sample to derive the silver content within the specimen S being tested. The basic principle in making this derivation is that the higher the silver content in the silver specimen S, the faster the silver oxide layer grows from the deposit of electrolyte from the pen probe 11. Therefore, the faster the rate of increase in the $I_{sense}$ current, the greater the percentage of silver in the specimen S. Preferably, the apparatus 10 will take eight readings of the current $I_{sense}$ before the testing of the specimen S is completed.

Presently, calibration of the apparatus 10 is desired after every four or five tests of specimens S. Calibration is conducted by utilizing a known silver content test specimen S, such as a 92.5% sterling silver specimen. The calibration button 26 is pressed to begin the calibration sequence so that the apparatus 10 knows to save the test results in the microprocessor 40 for comparison with the subsequent tests of the unknown silver specimens S. Thus, the count down set 39 of LEDs provides a visual indication as to how many unknown test specimens can be tested before a re-calibration of the apparatus 10 is needed. Built into the microprocessor 40 can be a block on further testing of unknown specimens S once the count down has diminished to zero, unless a calibration sequence is conducted.

Once a test of a silver specimen S has been conducted, the pen probe 11 has to be discharged of residual current, i.e. cooled down, before another test can be conducted. Presently, that cool down period is approximately 6-8 seconds, which can be programmed also into the microprocessor 40 to prevent any testing unless the cool down period has expired and the ready light 27 is illuminated. Thus, the power supply to the pen probe 11 is preferably modulated between on and off by the microprocessor 40 with the power being turned off for the cool down period.

In operation, the apparatus 10 is powered on through either an internal battery (not shown) or by a connection to a AC power source to provide, preferably, a 3.3 volt connection at the power input point 28. First, the apparatus 10 must be calibrated by depressing the calibration button 26 and placing a known silver content specimen S, such as a sterling silver (92.5% silver content) specimen, on the pan 25. The fiber tip 16 of the pen probe 11 is then pressed against the known specimen S to deposit electrolyte on the specimen S while the current $I_{pan}$ is passed through the pan 25, silver specimen S and pen probe 11. The apparatus 10 takes preferably eight readings of the current $I_{sense}$ to determine a rate of change of the current $I_{sense}$, which is proportional to the rate of growth of the silver oxide layer forming on the known silver specimen S due to the chemical reaction with the electrolyte. Once the eight readings have been completed, the microprocessor 40 stores the average rate of change in current $I_{sense}$ as the calibration sample for future comparisons.

Once calibrated, the pen probe 11 is passed through a cool down period by the microprocessor 40 turning the power off, before the apparatus 10 is ready to conduct a test of an unknown specimen S. When the ready light 27 is illuminated, the unknown silver content specimen S is placed onto the pan 25 and the fiber tip of the pen probe 11 is placed against the specimen S to deposit electrolyte thereon. As with the calibration procedure, the apparatus 10 takes eight readings of the $I_{sense}$ current and calculates an average rate of increase in the current $I_{sense}$ over the eight readings. Because the rate of growth of the silver oxide layer is proportional to the concentration of silver in the unknown test specimen S, the rate of increase in the current $I_{sense}$ will be reflective of the purity of the silver specimen. The rate of increase in the current $I_{sense}$ is then compared to the calibration reading stored in the microprocessor 40 and the purity of the silver is derived.

After the test of the unknown silver content specimen S has been completed, the microprocessor 40 again shuts off the power to the pen probe 11 so that the accumulated charge therein can be dissipated and the pen probe 11 cooled down. After the requisite cool down period, the microprocessor 40 illuminates the ready light 27 and another test of an unknown silver content specimen S can be conducted as described above. For each test of an unknown silver content specimen S, the count down LED set 39 is manipulated until ultimately reaching zero, whereupon a new calibration of the apparatus 10 is to be conducted, as described above, to enable another series of testing of unknown silver content specimens.

One skilled in the art will recognize that this principle of comparing the rate of increase, as opposed to simply measuring a voltage generated, of the growth of a resistive layer being formed on a test specimen can be extended to any precious metal specimen that can grow a resistive layer. Thus, while the preferred embodiment of the instant invention is described above with respect to testing for the purity of silver in an unknown silver content specimen, the same principle can be used to test for other precious metals, including gold.

It will be understood that changes in the details, materials, steps and arrangements of parts which have been described and illustrated to explain the nature of the invention will occur to and may be made by those skilled in the art upon a reading of this disclosure within the principles and scope of the invention. The foregoing description illustrates the preferred embodiment of the invention; however, concepts, as based upon the description, may be employed in other embodiments without departing from the scope of the invention.

Having thus described the invention, what is claimed is:

1. A method of determining the content percentage of silver within a specimen containing silver, comprising the steps of:
   providing a testing apparatus having a microprocessor, a source of electrical current, and an electrical circuit including a pen probe having a supply of a corrosive electrolyte, said electrical circuit having a fixed resistance circuit path and a variable resistance circuit path;
   depositing said electrolyte from said pen probe onto said specimen to create a growing electrically resistive layer between the pen probe and the specimen, said electrically resistive layer having a rate of growth;
   measuring a flow of electrical current through at least one of said circuit paths as said electrically resistive layer accumulates;
   ascertaining a rate of change in said flow of electrical current through at least one of said circuit paths; and
   utilizing the rate of change in said flow of electrical current through said variable resistance circuit path to define the content percentage of silver within said specimen, the rate of growth of said electrically resistive layer being proportional to the content percentage of silver within said specimen, said growing electrically resistive layer decreasing the flow of electrical current through said variable resistance circuit path which contains said specimen.

2. The method of claim 1 wherein said utilizing step includes the steps of:
   storing in a microprocessor within said testing apparatus a look-up table plotting various rates of change in electrical current flow against corresponding content percentages; and
   matching the ascertained rate of change in said flow of electrical current through at least one of said circuit paths to a plotted rate of change in electrical current flow in said look-up table to define the corresponding content percentage of the precious metal in said specimen.

3. The method of claim 2 wherein measuring step is accomplished multiple times before said ascertaining step, said ascertaining step providing an averaged rate of change in said flow of electrical current through at least one of said circuit paths for use in said matching step.

4. The method of claim 1 wherein said depositing step creates silver oxide to form said growing electrically resistive layer due to the corrosion of said electrolyte on the silver in said specimen.

5. A method of determining the content percentage of a precious metal within an unknown specimen containing said precious metal, comprising the steps of:
   providing a testing apparatus having an electrical circuit including a pen probe, said electrical circuit having a fixed resistance circuit path and a variable resistance circuit path;
   depositing an electrolyte from said pen probe onto said specimen to create a growing resistive layer between the pen probe and the specimen, said specimen and said growing resistive layer being in said variable resistance circuit path;
   determining the rate of growth of said resistive layer by measuring the flow of electrical current through said variable resistance circuit path and ascertaining a rate of change of the flow of electrical current through said variable resistance circuit path as said resistive layer grows, the rate of flow of electrical current through said resistive layer being proportionate to the rate of growth of said resistive layer; and
   comparing the rate of growth of said resistive layer to a rate of growth of a corresponding resistive layer on a calibration test sample; and
   deriving from said comparing step the concentration of said precious metal in said unknown specimen.

6. The method of claim 5 wherein said comparing step includes the steps of:
   storing in a microprocessor within said testing apparatus a look-up table plotting various rates of change in electrical current flow against corresponding content percentages;
   matching the ascertained rate of change in said flow of electrical current through at least one of said circuit paths to a plotted rate of change in electrical current flow in said look-up table to define the corresponding content percentage of the precious metal in said specimen; and
   displaying the results from said matching step on said testing apparatus.

7. The method of claim 6 wherein said measuring step is accomplished multiple times before said ascertaining step, said ascertaining step providing an averaged rate of change in said flow of electrical current through at least one of said circuit paths for use in said matching step.

8. The method of claim 6 further comprising the step of:
   terminating the flow of electrical current through said pen probe after said matching step to dissipate any accumulated electrical charge before conducting subsequent testing on a new specimen.

9. A testing apparatus for determining the content of precious metal within a specimen being tested, comprising:
   a meter including:
      a microprocessor having a memory;
      a source of electrical current connected to said microprocessor;
      an electrically conductive test pad;
      an indicator bar operably coupled to said microprocessor;
      an electronic circuit interconnecting said microprocessor, said indicator bar, said source of electrical current and said test pad;
   a pen probe connectable to said meter and said electronic circuit, said pen probe including:
      a non-conductive casing;
      a reservoir containing a supply of a corrosive electrolyte operable to create a resistive layer on said specimen when applied thereto due to corrosion of said precious metal in said specimen;
      said electronic circuit configured to establish two circuit paths for the flow of current with a fixed resistance circuit path and a variable resistance circuit path including said test pad, said object being tested when placed on said test pad, and said pen probe deposits said electrolyte on said specimen creating said resistive layer between said pen probe and said specimen, said microprocessor configured to identify a change in the rate of electrical current passing through said variable resistance circuit path as said resistive layer accumulates, the formation of said resistive layer being proportionate to the percentage of said precious metal in said specimen being tested.

10. The testing apparatus of claim 1 wherein said pen probe includes a tip supported in said casing and having a first end coupled to said reservoir to receive electrolyte therefrom and a second end exposed from said casing for engagement with said specimen.

11. The testing apparatus of claim 1 wherein said microprocessor includes a look-up table plotting various rates of change in the flow of electrical current versus a corresponding percentage content of said precious metal, said microprocessor being operable to compare the determined change in the rate of electrical current passing through said variable resistance circuit path as said resistive layer accumulates with the rates of change in the flow of electrical current is said look-up table to ascertain the corresponding percentage content of said precious metal within said specimen.

12. The testing apparatus of claim 11 wherein the ascertained corresponding percentage content of said precious metal within said specimen is displayed on said indicator bar.

13. The testing apparatus of claim 12 wherein said indicator bar includes a plurality of light emitting diode (LED) lights that are selectively illuminated by said microprocessor to reflect the ascertained corresponding percentage content of said precious metal within said specimen.

14. The testing apparatus of claim 13 wherein said microprocessor measures the electrical current flowing through one or more circuit paths at least eight times before determining the rate of change of the flow of electrical current through said specimen.

15. The testing apparatus of claim 14 wherein said microprocessor averages the rates of change of flow of electrical current through said specimen derived from the measurements of the electrical current flowing through one or more circuit paths before using an averaged rate of change to compare to said look-up table.

* * * * *